United States Patent [19]

Sommer et al.

[11] Patent Number: 5,407,913

[45] Date of Patent: Apr. 18, 1995

[54] METHOD AND COMPOSITION FOR SYSTEMIC TREATMENT OF TISSUE INJURY

[75] Inventors: Andreas Sommer, Concord; Christopher A. Maack, El Cerrito, both of Calif.

[73] Assignee: Celtrix Pharmaceuticals, Inc., Santa Clara, Calif.

[21] Appl. No.: 984,936

[22] Filed: Dec. 3, 1992

[51] Int. Cl.$^6$ ..................... A61K 37/36; A61K 31/56; A61K 33/16

[52] U.S. Cl. ........................................ 514/121; 514/21

[58] Field of Search ........................ 514/3, 4, 12, 21

[56] References Cited

U.S. PATENT DOCUMENTS

| | | | |
|---|---|---|---|
| 4,783,524 | 11/1988 | Larsen | 530/350 |
| 5,187,151 | 2/1993 | Clark | 514/12 |

FOREIGN PATENT DOCUMENTS

| | | |
|---|---|---|
| 0289314A2 | 11/1988 | European Pat. Off. . |
| 0434625A2 | 6/1991 | European Pat. Off. . |
| WO89/08667 | 9/1989 | WIPO . |
| WO92/18154 | 10/1992 | WIPO . |

OTHER PUBLICATIONS

Baxter, *Comp. Biochem. Physiol.*, vol. 91B(2), 229–235, 1988.

Baxter in Modern Concepts of Insulin–Like Growth Factors, edited by Spencer, Elsenior Science Publishing Co., Inc., 1991, pp. 371–380.

Blum et al., *Endocrinology*, 125(2), 766–772, 1989.

Gartner, M. H., et al., "Insulin–Like Growth Factors I and II Expression in the Healing Wound", *J. Surg. Res.* (1992) 52:389–394.

Skottner, A., et al., "Tissue Repair and IGF–I", *Acta Pediatr. Scand. (Suppl.)* (1988) 347:110–112.

Coates, C. L., et al., "Somatomedin Activity in Plasma From Burned Patients With Observations on Plasma Cortisol", *Burns* (1981) 7:425–433.

Cunningham, J. J., et al., "Plasma Somatomedin–C as an Index of Nutritional Status Following Burn Trauma and Chronic Malnutrition", *Proceedings of the American Burn Association, 18 Annual Meeting* (9–12 Apr. 1986, Chicago, IL), vol. 18, p. 128.

Moller, S., et al., "Insulin–Like Growth Factor 1 (IF-G–1) in Burn Patients", *Burns (1991) 17:279–281*.

Strock, L. L., et al., "The Effect of Insulin–Like Growth Factor I on Postburn Hypermetabolism", *Surgery* (1990) 108:161–164.

Sara, V. R., et al., "The Influence of Early Nutrition on Growth and the Circulating Levels of Immunoreactive Somatomedin A", *J. Develop. Physiology* (1979) 1:343–350.

Hansson, H. A., et al., "Evidence Indicating Trophic Importance of IGF-I in Regenerating Peripheral Nerves", *Acta Physiol. Scand.* (1986) 126:609–614.

D'Ercole, A. J., "Somatomedins/Insulin–Like Growth Factors and Fetal Growth", *J. Develop. Physiology* (1987) 9:481–495.

Brewer, M. T., et al., "Cloning, Characterization, and Expression of a Human Insulin–Like Growth Factor Binding Protein", *Biochem. Biophys. Res. Comm.* (1988) 152(3):1289–1297.

Hintz, R. L., et al., "A Sensitive Radioimmunoassay for Somatomedin–C/Insulin–Like Growth–Factor I Based on Synthetic Insulin–Like Growth Factor 57–70", *Horm. Metabol. Res.* (1988) 20:344–347.

Baxter, R. C., "The Insulin–Like Growth Factors and Their Binding Proteins", *Comp. Biochem. Physiol.* (1988) 91B:229–235.

Sjöberg, J., et al., "Insulin–Like Growth Factor (IG-F–1) as a Stimulator of Regeneration in the Freeze-In- (List continued on next page.)

*Primary Examiner*—Howard E. Schain
*Assistant Examiner*—Lynn Touzeau
*Attorney, Agent, or Firm*—Morrison & Foerster

[57] ABSTRACT

This is a method for enhancing systemic tissue repair in patients with burns, trauma and peptic ulcers, as well as patients about to undergo, is undergoing or just having undergone surgery. The method comprises systemically administering to such individuals a therapeutic composition comprising IGF and IGFBP. The preferred form is IGF-I/IGFBP-3.

28 Claims, No Drawings

OTHER PUBLICATIONS jured Rat Sciatic Nerve", *Brain Research* (1989) 485:102–108.

Daughaday, W. H., et al., "Insulin–Like Growth Factors I and II. Peptide, Messenger Ribonucleic Acid and Gene Structures, Serum, and Tissue Concentrations", *Endocrine Reviews* (1989) 10(1):68–91.

Binkert, C., et al., "Cloning, Sequence Analysis and Expression of a cDNA Encoding a Novel Insulin–Like Growth Factor Binding Protein (IGFBP-2)", *The EMBO Journal (1989) 8(9):2497–2502.*

Busby, W. H., et al., "Purification of a 31,000–Dalton Insulin–Like Growth Factor Binding Protein from Human Amniotic Fluid", *J. Biol. Chem.* (1988) 263(28):14203–14210.

Elgin, R. G., et al., "An Insulin–Like Growth Factor (IGF) Binding Protein Enhances The Biologic Response to IGF-I", *Proc. Natl. Acad. Sci.* (1987) 84:3254–3258.

Blum, W. F., et al., "Plasma IGFBP-3 Levels as Clinical Indicators", in *Modern Concepts in Insulin–Like Growth Factors*, E. M. Spencer, editor, (published by Elsevier, N.Y., 1991) pp. 381–393.

Wood, W. I., et al., "Cloning and Expression of the Growth Hormone–Dependent Insulin–Like Growth Factor–Binding Protein", *Mol. Endocrin.* (1988) 2:1176–1185.

Spratt, S. K., et al., "Cloning and Expression of Human Insulin–Like Growth Factor Binding Protein 3", *Growth Factors* (1990) 3:63–72.

Martin, J. L., et al., "Insulin–Like Growth Factor–Binding Protein From Human Plasma", *J. Biol. Chem.* (1986) 261(19):8754–60.

Sommer, A., et al., "Molecular Genetics and Actions of Recombinant Insulin–Like Growth Factor Binding Protein-3", in *Modern Concepts in Insulin–Like Growth Factors*, E. M. Spencer, editor, (published by Elsevier, N.Y., 1991) pp. 715–728.

Shimasaki, S., et al., "Identification and Molecular Characterization of Insulin–Like Growth Factor Binding Proteins", *Prog. Growth Factor Res.* (1991) 3:243–266.

Spencer, E. M., et al., "Somatomedins: Do They Play a Pivotal Role in Wound Healing?", in *Growth Factors and Other Aspects of Wound Healing: Biological and Clinical Implications* (1988), pp. 103–116.

Jennische, E., et al., "Dynamic Changes in Insulin–Like Growth Factor I Immunoreactivity Correlate to Repair Events in Rat Ear After Freeze-Thaw Injury", *Epx. Mol. Pathol.* (1987) 47:193–201.

METHOD AND COMPOSITION FOR SYSTEMIC TREATMENT OF TISSUE INJURY

DESCRIPTION

1. Technical Field

This invention relates to a treatment to aid tissue repair. This invention is a medical treatment for individuals who are undergoing surgery or who have burns, peptic ulcers, or traumatic injuries. The treatment comprises systemic administration of a therapeutic composition of insulin-like growth factor-I (IGF-1) and insulin-like growth factor: binding protein-3 (IGFBP-3).

2. Background Art

Growth Factors

Growth factors are polypeptides which stimulate a wide variety of biological responses (e.g., DNA synthesis, cell division, cell differentiation, expression of specific genes, etc.) in a defined population of target cells. A variety of growth factors have been identified including transforming growth factor-$\beta_1$ (TGF-$\beta_1$), TGF-$\beta_2$, TGF-$\beta_3$, epidermal growth factor (EGF), platelet-derived growth factor (PDGF), fibroblast growth factor (FGF), insulin-like growth factor-I (IGF-I), and IGF-II.

IGF-I and IGF-II are related in amino acid sequence and structure, with each polypeptide having a molecular weight of approximately 7500 daltons. IGF-I mediates the major effects of growth hormone and thus is the primary mediator of skeletal growth after birth. IGF-I has also been implicated in the actions of various other growth factors, since treatment of cells with such growth factors often leads to increased production of IGF-I. In contrast, IGF-II is believed to have a major role in fetal growth. Both IGF-I and IGF-II have insulin-like activity (hence the name) and are mitogenic (stimulating cell division) for various cell types involved in the growth and differentiation of cells involved in wound healing.

IGF can be measured in blood serum to diagnose abnormal growth-related conditions, e.g., pituitary gigantism, acromegaly, dwarfism, various growth hormone deficiencies, etc. Although IGF is produced in many tissues, most circulating IGF is believed to be synthesized in the liver.

Unlike most growth factors, the IGFs are present in substantial quantity in the circulation, but only a very small fraction of this IGF is free in the circulation or in other body fluids. Most IGF is complexed with IGF-binding proteins. IGF in the blood is mainly complexed with IGFBP-3, the major circulating IGF-binding protein.

Almost all IGF circulates in a non-covalently associated ternary complex composed of IGF-I or -II, an IGF specific binding protein termed IGFBP-3, and a larger protein termed the Acid Labile Subunit (ALS). This ternary complex is composed of equimolar amounts of each of the three components. The ALS has no direct IGF binding activity and appears to bind only a preformed IGF/IGFBP-3 complex. The ternary complex of IGF+IGFBP-3+ALS has a molecular weight of approximately 150,000 daltons. This ternary complex likely functions in the circulation "as a reservoir and a buffer for IGF-I and IGF-II, preventing rapid changes of free IGF." Blum, W. F., et al., "Plasma IGFBP-3 Levels as Clinical Indicators", In *Modern Concepts in Insulin-Like Growth Factors*, E. M. Spencer, ed., Elsevier, New York, pages 381–393, 1991.

Having most circulating IGF in complexes is very beneficial. Excess free IGF can cause serious hypoglycemia because IGF has insulin-like effects on circulating glucose levels. In contrast to the low levels of free IGFs and IGFBP-3, there is a substantial pool of free ALS in plasma which assures that IGF/IGFBP-3 complex entering the circulation immediately forms a ternary complex.

IGF Binding Proteins

IGFBP-3 is the most abundant IGF binding protein in the circulation. Recently, Wood et al. (*Mol. Endocrin.* (1988), 2:1176-85) and Spratt et al. (*Growth Factors* (1990), 3:63–72) described the cloning and expression of human IGFBP-3. The gene for IGFBP-3 codes for 291 amino acids, the first 27 of which represent a characteristic signal sequence. Thus, the mature protein comprises 264 amino acids and has a calculated molecular weight of 28,749 (without glycosylation or other post-translational modifications). When the human IGFBP-3 gene was expressed in Chinese hamster ovary (CHO) cells and the conditioned culture medium was subjected to SDS electrophoresis and transferred to nitrocellulose membrane, Spratt et al. reported "the presence of a 43–45-kd doublet [protein band], a 28 kd band and a minor 31 kd band, indicating there were posttransitional changes." (p. 69) This pattern is seen in serum, suggesting a similar range of post-translational changes.

It is unclear which tissue is the primary source of circulating IGFBP-3, although synthesis has been demonstrated in numerous cell types, including human fibroblasts, liver cells (most likely Kupfer cells) and osteoblasts. IGFBP-3 cDNA has been identified in cDNA libraries obtained from liver and other tissues. Vascular endothelial cells produce IGFBP-3 and may be the major source for systemic IGFBP-3.

IGFBP-3 has been purified from natural sources and produced by recombinant means. For instance, IGFBP-3 can be purified from natural sources using a process such as that shown in Martin and Baxter, (*J. Biol. Chem.* (1986) 261:8754-60). IGFBP-3 can be synthesized by recombinant organisms as discussed in Sommer, A., et al., In *Modern Concepts of Insulin-Like Growth Factors*, E. M. Spencer, ed., Elsevier, N.Y., pp. 715–728, 1991. This recombinant IGFBP-3 binds IGF-I with a 1:1 molar stoichiometry.

At least five other distinct IGF binding proteins have been identified in various tissues and body fluids. Although all these proteins bind IGFs, they each originate from separate genes and they have distinct amino acid sequences. Thus, the binding proteins are not merely analogs of a common precursor. For example, Spratt et al. compared the amino acid sequences of IGFBP-1, -2 and -3. Of the total 264 amino acids in the mature protein, only 28% of the amino acids are identical between IGFBP-3 and IGFBP-1, and 33% are identical between IGFBP-3 and IGFBP-2. Spratt et al. suggested that the similar portions of the binding proteins are the region(s) that bind IGF. Unlike IGFBP-3, the other IGFBPs in the circulation are not saturated with IGFs. It appears that the lower saturation of the other IGFBPs in the circulation is due to excess binding capacity. None of the IGF binding proteins other than IGFBP-3 can form the 150 kd circulating ternary complex. All six known IGF binding proteins are reviewed and compared by Shimasaki and Ling, *Prog. Growth Factor Res.* (1991) 3:243-66.

Wound Healing Following Surgery or Trauma

Numerous investigators have reported higher levels of IGF in injured tissue (Spencer et al. *Growth Factors and Other Aspects of Wound Healing* (1988), pp. 103-16 (surgical wound and implanted wound canister); Jennische et al. *Exp. Mol. Pathol.* (1987) 47:193-201 (freeze-thaw injury); Gartner et al. *J. Surg. Res.* (1992) 52:389-94 (implanted sponge and controlled length scar models; high levels of expression of IGF-1 and IGF-2 mRNA in wounds after 1 day). Skottner et al. *(Acta Pediatr. Scand, [Suppl.]* (1988) 347:110-12) reported that local application of IGF-1 to a crush lesion of rat sciatic nerve significantly increased nerve regeneration which could be inhibited by anti-IGF-1 antibodies.

Drop et al. (WO89/08667), after disclosing an amino acid sequence for IGFBP-1 and its recombinant production, briefly mention that this binding protein could be administered with a variety of growth factors, including IGF-1 and IGF-2, either locally or systemically. Drop et al. further proposed that such formulations could be used in healing wounds and treating osteoporosis.

Wound Healing in Burn Patients

In patients with severe burns, the IGF-1 level is low (Coates et al., *Burns* (1981) 7:425; Cunningham et al., *Proc. Amer. Burn Assoc.* (1986) 18:128). Moller et al. (*Burns* (1991) 17: 279- 81) correlated the decreased IGF-1 level with the surface area of the burn and proposed that the low level may be due to IGF diffusion from the burned ,skin. The reduced IGF level persisted for about 3-4 weeks after large burns. Moller et al. proposed that the reduced "IGF-1 concentration may contribute to the reduced wound healing." (page 280)

Strock et al. *(Surgery* (1990) 108:161-64) studied the effects of IGF administration on Sprague-Dawley rats which were given a full-thickness burn over one half of the body surface area. After the burn, osmotic pumps administering 1000 μg/day of IGF were implanted in the rats. Circulating IGF levels decreased markedly after the burn before the pumps were implanted. Body weight increased significantly for IGF-treated burned rats, particularly in comparison with the burned rats not receiving IGF, even though control rate were fed the same amount as IGF-treated rats. The increase in body weight was interpreted as "a direct anabolic effect of IGF-I in the postinjury state." (page 163)

Wound Healing with Glucocorticoid Therapy

In EP 0 434 625 A2 publication dated 26 Jul. 1991, Goldberg disclosed the administration of IGF-1 either alone to counteract the effect of endogenous corticosteroids or the administration of IGF-1/glucocorticoid cocktails, wherein IGF-1 would blunt the deleterious effect of steroids on cartilage and wound repair, particularly in osteoarthritis.

The prior art has not suggested that systemic administration of the combination of IGF and IGFBP could aid in burn healing, in recovery from surgical wounds, or in wound healing impaired by steroid administration.

Disclosure of Invention

In accordance with one embodiment of the present invention, there is provided a method for enhancing tissue repair in an individual who is about to undergo, is undergoing or has just undergone surgery. The method provides for systemic administration to the individual of a therapeutic composition including insulin-like growth factor (IGF) and insulin-like growth factor binding protein (IGFBP) in quantities sufficient to enhance tissue repair and accelerate healing.

In accordance with another embodiment of the present invention, the individual undergoing surgery is having a tumor resected, is having an organ or body part removed or replaced, is receiving glucocorticoid therapy or is diabetic.

In accordance with a further embodiment of the present invention, the mode of systemic administration can be parenteral or gastrointestinal. Parenteral forms of administration include subcutaneous, intravenous intraperitoneal and intramuscular injection.

In yet another embodiment, the method of the present invention provides IGF as IGF-I. In a further embodiment, the IGF-I is recombinant human IGF-I.

In yet another embodiment, the method of the present invention provides IGFBP as IGFBP-3. In a further embodiment, the IGFBP-3 is recombinant human IGFBP-3.

In another embodiment, the individual to whom the therapeutic composition is administered is a mammal.

In yet another embodiment, the method provides for administration of the IGF/IGFBP composition in an amount of about 0.01 to 5 mg of IGF/kg/day bound to an approximately equimolar amount of IGFBP-3.

In accordance with another embodiment of the present invention, there is provided a method for treating a burned individual to enhance healing of the burn. The method provides for systemic administration to the individual of a therapeutic composition including insulin-like growth factor (IGF) and insulin-like growth factor binding protein (IGFBP) in a quantity sufficient to enhance healing of the individual's burn.

In accordance with still another embodiment of the present invention, there is provided a method for treating an individual who has experienced traumatic injuries to enhance repair of hard and soft tissue. The method provides for systemic administration to the individual of a therapeutic composition including insulin-like growth factor (IGF) and insulin-like growth factor binding protein (IGFBP) in a quantity sufficient to enhance healing of the individual's injuries.

In accordance with still another embodiment of the present invention, there is provided a method for treating an individual who has a peptic ulcer to enhance healing of the ulcer. The method provides for systemic administration to the individual of a complex including insulin-like growth factor (IGF) and insulin-like growth factor binding protein (IGFBP) in a quantity sufficient to enhance healing of the individual's peptic ulcer.

While not wishing to be bound by any particular theory, the Inventors propose that the systemically administered IGF and IGFBP composition first raises the blood level of IGF/IGFBP. The IGF is then carried to the regenerating tissues via the circulation.

Modes For Carrying Out the Invention

Definitions:

As used herein, "Insulin-like growth factor (IGF)" comprises a family of factors, including but not limited to IGF-I and IGF-II. IGF is a polypeptide having a molecular weight of about 7500 daltons. IGF can be obtained from natural sources or prepared by recombinant means. The term "IGF" also includes active fragments of IGF, elongated forms of IGF (with added amino acids or carbohydrates), and modified forms of IGF (resulting from natural mutation of the recombinant source or conservative substitutions of amino acids).

"Insulin-like growth factor binding protein (IGFBP)" comprises a family of binding proteins, including but not limited to IGFBP-1, IGFBP-2, IGFBP-3, IGFBP-4, IGFBP-5 and IGFBP-6. IGFBP can be obtained from natural sources or prepared by recombinant means. At least one form of IGFBP (for example, IGFBP-3) complexes with IGF and with a third molecule known as ALS. The term "IGFBP" includes glycosylated and non-glycosylated forms of the proteins.

A "therapeutic composition" as used herein is defined as comprising IGF complexed with its binding protein IGFBP-3. The therapeutic composition may also contain excipients such as water, minerals and carriers such as protein.

"Systemic administration" is any method of administration to an animal as a whole. It does not include local application of the complex directly onto a wound. Systemic administration includes parenteral and gastrointestinal and nasal routes. The parenteral route includes a wide variety of administration methods, including intravenous, subcutaneous, intraperitoneal and intramuscular routes. The gastrointestinal route includes oral, enteral and rectal administration.

"Individuals" are defined as humans and mammalian farm animals, sport animals and pets. Farm animals include, but are not limited to, cows, hogs, and sheep. Sport animals include, but are not limited to, dogs and horses. The category pets includes, but is not limited to, cats and dogs.

The method of the present invention contemplates enhancing systemic tissue repair, nitrogen balance and immune function in a variety of conditions, including, but not limited to, individuals about to undergo, undergoing or having undergone surgery, individuals with burns; individuals with traumatic injuries; and individuals with peptic ulcers, by administering a therapeutic composition of IGF/IGFBP.

Individuals undergoing surgery often have difficulty maintaining a positive nitrogen balance. This can interfere with the body's healing processes. If insufficient nutrients are available or inefficiently marshaled, healing is inefficient, and hospital stays may be prolonged.

Some individuals have more difficulty healing after surgery, particularly individuals with tumors, individuals receiving glucocorticoids and diabetics.

Individuals with cancer may be wasted and in negative nutritional balance prior to surgery. Without extra supportive medical care, healing after tumor resection may be slow or even incomplete. Administration of the IGF/IGFBP complex aids healing.

Diabetics who undergo surgery often heal slowly or inadequately. During surgery, stress causes high plasma levels of cortisol, which antagonizes the effect of insulin. Therefore, insulin-requiring diabetics require more insulin during surgery. Typically, the physician gives such the diabetic ⅓ to ½ of a normal daily insulin dose before surgery. As the diabetic recovers from surgery, the insulin dose is repeated. In the meantime, 5% glucose solution is slowly infused and adjusted to maintain blood sugar levels. Administration of IGF/IGFBP beginning before surgery would increase the blood level of IGF and should aid in overcoming the effects of cortisol. IGF/IGFBP can enhance healing in the post-surgical diabetic, both by its direct effect on the healing process and by its insulin-like effects on glucose utilization.

Individuals who have been on glucocorticoid therapy prior to surgery can benefit from the administration of the IGF/IGFBP composition. Glucocorticoids include, but are not limited to, cortisol, prednisolone, triamcinolone, dexamethasone, beclomethasone, betamethasone, and budesonide. Cortisol and its analogs suppress the inflammatory response and also suppress fibroblast proliferation and collagen deposition. These actions impair wound healing. Because of these actions, peptic ulcers and capillary fragility are occasional side effects of steroid administration. Administration of the IGF/IGFBP composition can overcome these deleterious effects of glucocorticoids.

After prolonged administration, abrupt withdrawal of steroid can cause a life-threatening condition because normal adrenal function has been suppressed and is insufficient. Administration of the IGF/IGFBP complex helps counteract the negative effects of steroids on individuals undergoing surgery and permits the physician to gradually withdraw steroid therapy. In such cases, the IGF/IGFBP composition also can enhance wound healing.

Burn sufferers can benefit from administration of the IGF/IGFBP complexes. Burn patients have wounds to heal. The complex delivers IGF in a gradual manner to aid healing without causing hypoglycemia.

Peptic ulcers occur in individuals receiving some anti-inflammatory drugs and in numerous other individuals. Peptic ulcers are related in part to acid secretion; however, most individuals secrete stomach acid but few have ulcers. Peptic ulcers probably arise when the gastrointestinal mucosal lining does not replace itself quite rapidly enough. Acid erosion then progresses through the mucosa into the submocosal layer and even into the muscular layer. Peptic ulcers may occur in the stomach (gastric) or in the upper intestine (duodenal). In the same way that IGF/IGFBP encourages wound healing in other areas, IGF/IGFBP can help heal peptic ulcers.

The formulation, method of administration and dosage will depend upon the disorder to be treated, and the medical history of the patient. These factors are readily determinable in the course of therapy. Suitable patients with burns or trauma, ulcers, or a need for surgery can be identified by medical history, physical findings and laboratory tests.

In accordance with the method of the present invention, the formulation comprises a complex of IGF and IGFBP. Preferably, the IGF is IGF-I, although IGF-II can be useful. In another embodiment, IGF can be a mixture of IGF-I and IGF-II. In such a mixture, the ratio of IGF-I to IGF-II ranges from 0.01 to 99.

IGFBP can be any of IGFBP-1, -2, -3, -4, -5 or -6. IGFBP also can be a mixture of any combination of the six IGFBP's. Such a mixture would take advantage of the different binding affinities for IGF-I and IGF-II, ability of some IGFBP's to bind to cell surfaces, and different half-lives.

The molecular structure of IGFBP-1 was disclosed by Brewer et al., *Biochem. Biophys. Res. Comm.* (1988) 152(3):1289–1297 and by Drop et al. in PCT Publication No. WO 89/98667, published on Sep. 21, 1989. Human IGFBP-1 has 234 amino acids and a molecular weight of about 28 kd. In combination with IGF-I, IGFBP-1 seems to stimulate thymidine incorporation into cellular DNA. Busby et al., *J. Biol. Chem.* (1988) 263:14203-10;

Elgin et al., *Proc. Natl. Acad. Sci. USA* (1987) 84:3254-58. Droplet al. (ibid.) suggested that IGFBP-1 would be useful in tissue repair because of its potentiation of growth of connective tissue and muscle cells.

IGFBP-2 comprises 289 amino acids (human) and has a molecular weight of 36 kd under nonreducing conditions. The amino acid sequence of human IGFBP-2 was determined from cDNA clones isolated from a human fetal liver library by Binkerr et al. *EMBO J.* (1989) 8:2493-2502. IGFBP-2 also may bind to cell surfaces. IGFBP-2 has a preference for IGF-II, and thus is preferred in formulations comprising IGF-II.

Preferably the IGFBP in the IGF/IGFBP complex is IGFBP-3. Native and recombinant IGFBP-3, as well as some N-terminal and C-terminal fragments, bind IGF-I and IGF-II. Human IGFBP-3 comprises 264 amino acids and has three potential N-linked glycosylation sites. IGFBP-3 is the major IGFBP in blood.

Nearly all IGF-I or IGF-II in blood is bound to IGFBP-3, and IGF/IGFBP-3 normally circulates in the form of a complex in humans and other mammals. This complex associates with a third protein (ALS), which is present in excess over the normal concentrations of IGF and IGFBP-3. Therefore, ALS is found both associated with the IGF/IGFBP-3 complex and in the free form. The resultant ternary complex has a size of about 150 kD. Administration of the complex of IGF and IGFBP-3, either obtained from natural or recombinant sources, results in the formation of the ternary complex with the normally excess ALS. This type of treatment appears to produce a long term increase in the level of circulating IGF, which is gradually released from the ternary or binary complex. This mode of administration avoids the detrimental side effects associated with administration of free IGF-I (e.g., hypoglycemia, suppression of growth hormone and ALS production, and release of endogenous IGF-II from endogenous IGFBP-3 since administered free IGF-I replaces endogenous IGF-II in normally circulating IGF-II/IGFBP-3 complexes).

IGFBP-4 and IGFBP-6 are glycosylated proteins which are widely distributed in the body. The primary structure of IGFBP-4 was reported by Shimasaki et al. *Mol. Endocrinol.* (1990) 4:1451-1458. IGFBP-6, whose cDNA has been isolated by Shimasaki et al. (*Mol. Endocrinol.* (1991) 4:938-48), has a much greater affinity for IGF-II than for IGF-I.

IGFBP-5 is a 252 amino acid binding protein which is not glycosylated. Shimasaki et al. (*J. Biol. Chem.* (1991) 266:10646-53) cloned human IGFBP-5 cDNA from a human placenta library.

Depending on the binding, metabolic and pharmacokinetic characteristics required in the IGF/IGFBP complex formulation, these binding proteins can be added to the complex formulation in various proportions. These IGFBP's can be combined in a wide variety of ratios with IGF-I and/or IGF-II.

Because IGF and IGFBP-3 naturally complex in a 1:1 molar ratio, a composition of equimolar amounts of IGF and IGFBP-3 is preferred. The product can be formulated with IGF:IGFBP-3 molar ratios ranging from 0.5 to 1.5. More preferably, the molar ratio is 0.9 to 1.3; and most preferably, the product is formulated with approximately a 1:1 molar ratio. When other IGFBP(s) are used, the ratio of IGFBP(s) to IGF can vary.

In accordance with the preferred method of the present invention, IGF and IGFBP are human proteins obtained from natural or recombinant sources. Most preferably, IGF and IGFBP are human IGF-I and IGFBP-3 made by recombinant means and designated rhIGF-I and rhIGFBP-3, respectively. rhIGFBP-3 can be administered in glycosylated or non-glycosylated form. *E. coli* is a source of the recombinant non-glycosylated IGFBP-3. Glycosylated IGFBP-3 can be obtained in recombinant form from Chinese hamster ovary (CHO) cells.

The method of the present invention provides for formulating the IGF/IGFBP composition in modes which are readily apparent to those skilled in the art. Preferably, the IGF and IGFBP are complexed prior to administration to the treated individual. Preferably, the complex is formed by mixing approximately equimolar amounts of IGF-I and IGFBP-3 dissolved in physiologically compatible carriers such as normal saline solution or phosphate buffered saline solution. Most preferably, a concentrated solution of rhIGF-I and a concentrated solution of rhIGFBP-3 are mixed together for a sufficient time to form an equimolar complex.

Depending on the mode of administration, the IGF/IGFBP composition is in the form of solid, semi-solid or liquid dosage preparations, such as for example, tablets, pills, powders, capsules, liquids, suspensions or the like. Dosage forms for gastrointestinal administration must be suitably coated and buffered to avoid gastrointestinal digestion of the proteins. Physiologically compatible carriers include intravenous solutions, such as normal saline, serum albumin, 5% dextrose, plasma preparations, other protein-containing solutions and TPN solutions. The preferred carrier for parenteral administration of the IGF/IGFBP composition is a sterile, isotonic aqueous solution, such as normal saline or 5% dextrose. Alternatively, a solution of the composition can be placed into an implant, such as an osmotic pump, for the slow release of the composition over an extended period of time. Alternatively, the composition can be provided in sustained release carrier formulations such as semi-permeable polymer carriers in the form of suppositories or microcapsules for systemic administration. See, for instance, U.S. Pat. No. 3,773,919 for Microcapsular Sustained Release Matrices Including Polylactides; Sidmon et al., *Biopolymers* 22 (1), 547-556 (1983) for copolymers of L-glutamic acid and γ-ethyl-L-glutamate; Langer et al., *J Biomed Res* 15, 167-277 (1981) for poly(2-hydroxyethylmethacrylate) or the like.

The mode of administration delivers the IGF/IGFBP composition systemically to the individual in a safe, physiologically effective manner. The composition can be given by subcutaneous, intravenous, intramuscular, intraperitoneal, or other conventional routes of administration. Preferably, the complex is injected subcutaneously, intravenously or intramuscularly. Another preferred mode of administration of the IGF/IGFBP complex is in a short-term intravenous infusion as, for example, during surgery or when the burned or traumatized individual is receiving other intravenous fluids. If the individual is not receiving intravenous fluids, the most preferred route of administration of IGF/IGFBP is subcutaneous injection. Preferably, IGF/IGFBP is administered as a slow-release subcutaneous depot injection. By subcutaneous injections the complex appears not to be toxic or mitogenic at the injection site. In another preferred mode of administration, IGF/IGFBP is administered by continuous intravenous infusion in combination with nutrient solutions such as TPN solutions.

The dose of IGF/IGFBP composition to be administered can be readily determined by those skilled in the art, based on the usual patient symptoms discussed above. Preferably, when IGF/IGFBP is administered as a complex to humans daily, the dosage of complex is at least about 0.05 mg IGF/kg of body weight/day, complexed to an approximately equimolar amount of IGFBP. More preferably, the daily dosage of the complex for humans is at least 0.1 mg IGF/kg/day, complexed to an approximately equimolar amount of IGFBP. If daily dosages in excess of about 0.5 mg IGF/kg must be given, the dosage can be divided and injected subcutaneously at two or more sites.

If the IGF/IGFBP complex were administered to humans twice a week, each dose of complex is preferably at least about 0.1 mg IGF/kg of body weight, complexed to an approximately equimolar amount of IGFBP. More preferably, for twice weekly administration, the dose of the complex is at least 0.5 mg IGF/kg, complexed to an approximately equimolar amount of IGFBP. There is no known upper limit of dosage; however, it is preferable that a single dose not exceed about 5 mg IGF/kg of body weight, when the IGF is complexed to an approximately equimolar amount of IGFBP. These doses of IGF/IGFBP complex are not expected to cause significant hypoglycemia since IGFBP prevents the acute presence of large amounts of free IGF and therefore the acute reduction of blood glucose levels.

Preferably, the patient about to undergo surgery is started with a relatively low dose of the complex, such as 0.05 mg of IGF-I complexed with an approximately equimolar amount of IGFBP-3/kg of body weight/day. Preferably, systemic administration of the complex begins at least several hours before surgery. Even more preferably, systemic administration begins about a day before surgery. Preferably, systemic administration of the IGF/IGFBP complex continues for at least several days and preferably as long as the healing period, which may last weeks.

Another preferred regimen provides for systemic administration of the IGF/IGFBP complex beginning on the day of surgery, trauma or burn and continuing treatment for at least several days to weeks.

Various factors should be monitored to determine if there is sufficient improvement and dosage. These include, but are not limited to, systemic IGF-I levels, nitrogen balance, weight, hand-grip strength, arm-muscle circumference, serum prealbumin, serum glucose, serum albumin, and the appearance of wounds, burns or ulcers. If the patient improves with the low dose, the low dose preferably should be continued until the patient sufficiently heals, as indicated by the physical findings and laboratory results described above. For example, the surgical wound or burn should be healing satisfactorily. Such improvement may be evident in two to three weeks.

If the indicator signs and symptoms do not improve promptly on the low dose of the complex, the dose preferably should be increased gradually until the signs and symptoms improve satisfactorily.

In the hospital, intravenous infusions and subcutaneous injections of the IGF/IGFBP complex are preferred. In the clinic or doctor's office, subcutaneous injections frequently are preferred.

Somewhat higher per kilogram doses are needed for small animals receiving the IGF/IGFBP complex. For example, a small dog can be dosed twice a week with about 0.05 to 1.0 mg of IGF/kg of body weight complexed with an equimolar amount of IGFBP.

The invention has been disclosed by direct description. The following are examples showing the efficacy of the method in systemic tissue repair. The examples are only examples and should not be taken in any way as limiting to the scope of the method.

EXAMPLES

Example 1

The effect of a systemically administered complex of IGF and IGFBP was tested on post-surgical healing of animals given the glucocorticoid methylprednisolone.

Sprague-Dawley rats weighing at least 350 grams were selected. On the back of each, four Hunt-Schilling wire mesh wound cylinders were implanted subcutaneously. Each animal was injected subcutaneously with 8 mg of methylprednisolone at the time of surgery. In addition, some rats were given daily subcutaneous injections at a site distant from the implanted wound cylinders of IGF-I or the complex of IGF-1 and IGFBP-3 (both supplied by Celtrix Pharmaceuticals, Santa Clara Calif.) in PBS and 0.1% rat serum albumin, pH 6.0. The treatment groups were

| Vehicle | (negative control) |
|---------|---------------------|
| IGF-I | 1.25 mg IGF-I/kg/day |
| Complex | 1.25 mg IGF-I/kg/day complexed with an equimolar amount of IGFBP-3 |

On postoperative day 17, the tissue in the wound cylinders was harvested and dried at 37° C. Dry weights, DNA, total protein and hydroxyproline (collagen) contents were obtain according to published procedures. Burton, *Biochem. J.* (1956) 17: 428–430; Grant, *J. Clin. Pathol.* (1964) 17: 685–686; and Moore and Stein, *J. Biol. Chem.* (1954) 211: 907–913.

When values from rats treated with IGF-I were compared with those of the negative control, wound cylinder dry weight increased 250%, DNA increased 340%, total protein increased 200% and hydroxyproline increased 205%. When the results in the animals treated with the complex of IGF-I and IGFBP-3 were compared with those of the negative control, wound cylinder dry weight increased 360%, DNA increased 450%, total protein increased 320% and hydroxyproline increased 250%. All values were significantly higher for the animals administered the complex of IGF-I and IGFBP-3 than for the IGF-I-treated animals.

This experiment indicates that the wound healing defect induced by glucocorticoid administration was reversed by the systemic administration of the complex of IGF-I and IGFBP-3.

Example 2

The effect of a systemically administered complex of IGF and IGFBP is tested on post-surgical healing of animals given skin wounds.

Young pigs weighing about 10 to 15 kg are fasted for at least six hours before surgery. Anesthesia is administered intravenously, along with a dose of vehicle, IGF-I alone or the complex of IGF-I and IGFBP-3. Under aseptic conditions, the pigs' backs and stomachs are clipped, shaved and washed. Then the area to be wounded is disinfected With 70% alcohol. Next a block of pig skin measuring 1 cm×1.5 cm×0.7 cm deep is removed. This depth involves all the epithelium and part of the dermis and is similar in depth to a second degree burn. The wounds are then dressed with sterile dressings, which are replaced daily. The animals receive daily subcutaneous doses of vehicle, IGF-I alone or the complex of IGF-I and IGFBP-3 for five days. On the seventh day, the healing wound is biopsied.

Histologic specimens are prepared using standard paraffin impregnating and embedding techniques. Four micron sections are made and stained using hematoxylin and eosin. Slides are marked with numbers which in a separate book are related to the test and control animals. Other investigators who did not prepare or number the slides measure the widths of epithelial and connective tissue layers under the microscope.

Wounds from animals treated with the complex of IGF-I and IGFBP-3 show the most improvement, followed by those of animals treated with IGF-I. The animals given the vehicle heal at the normal rate.

This invention has been detailed both by example and by direct description. It should be apparent that one having ordinary skill in this art would be able to surmise equivalents to the invention as described in the claims which follow but which would be within the spirit of the description above. Those equivalents are to be included within the scope of this invention.

We claim:

1. A method for enhancing wound healing in an individual about to undergo, undergoing or just having undergone surgery, said method comprising systemically administering to said individual a therapeutic composition comprising a complex of IGF-I and IGFBP-3, wherein the molar ratio of IGF-I to IGFBP-3 is in the range between 0.5:1 to 1.5:1 and said complex is administered in quantities sufficient to enhance wound healing in said individual.

2. The method of claim 1 wherein said individual undergoing surgery is having a tumor resected, is having an organ removed or replaced, is receiving glucocorticoid therapy or is diabetic.

3. The method of claim 1 wherein the systemic administration of the complex is either parenteral or gastrointestinal.

4. The method of claim 3 wherein said parenteral administration is selected from the group consisting of subcutaneous, intravenous, intraperitoneal and intramuscular injection.

5. The method of claim 1 wherein said IGF-I is recombinant human IGF-I.

6. The method of claim 1 wherein said IGFBP-3 is recombinant human IGFBP-3.

7. The method of claim 6 wherein recombinant human IGFBP-3 is non-glycosylated.

8. The method of claim 1 wherein said amount of IGF-I administered is about 0.1–5 mg of IGF-I/kg of body weight/day.

9. The method of claim 8 wherein IGF-I is complexed to an approximately equimolar amount of IGFBP-3.

10. The method of claim 1 wherein said individual is a mammal.

11. A method for treating an individual who has received a burn, said method comprising systemically administering to said individual a therapeutic composition comprising a complex of IGF-I and IGFBP-3, wherein the molar ratio of IGF-I to IGFBP-3 is in the range between 0.5:1 to 1.5:1 and said complex is administered in quantities sufficient to enhance healing of said burn in said individual.

12. The method of claim 11 wherein said systemically administering the composition comprises parenteral, gastrointestinal and nasal administration.

13. The method of claim 12 wherein said parenteral administration is selected from the group consisting of subcutaneous, intravenous, intraperitoneal and intramuscular injection.

14. The method of claim 11 wherein said IGF-I is recombinant human IGF-I.

15. The method of claim 11 wherein said IGFBP-3 is recombinant human IGFBP-3.

16. The method of claim 15 wherein said recombinant human IGFBP-3 is non-glycosylated.

17. The method of claim 11 wherein said amount of IGF-I administered is about 0.1–5 mg of IGF-I/kg of body weight/day.

18. The method of claim 17 wherein IGF-I is complexed to an approximately equimolar amount of IGFBP-3.

19. The method of claim 11 wherein said individual is a mammal.

20. A method for treating an individual who has been injured by trauma, said method comprising systemically administering to said individual a therapeutic composition comprising a complex of IGF-I and IGFBP-3, wherein the molar ratio of IGF-I to IGFBP-3 is in the range between 0.5:1 to 1.5:1 and said complex is administered in quantities sufficient to enhance healing of the traumatic injuries.

21. The method of claim 20 wherein said the systemic administration of the composition is either parenteral, gastrointestinal, or nasal.

22. The method of claim 21 wherein said parenteral administration is selected from the group consisting of subcutaneous, intravenous and intramuscular injection.

23. The method of claim 20 wherein said IGF-I is recombinant human IGF-I.

24. The method of claim 20 wherein said IGFBP-3 is recombinant human IGFBP-3.

25. The method of claim 24 wherein said recombinant human IGFBP-3 is non-glycosylated.

26. The method of claim 20 wherein said amount of IGF-I administered is about 0.1–5 mg of IGF-I/kg of body weight/day.

27. The method of claim 26 wherein IGF-I is complexed to an approximately equimolar amount of IGFBP-3.

28. The method of claim 20 wherein said individual is a mammal.

* * * * *